United States Patent [19]

Wiegner

[11] Patent Number: 4,662,876

[45] Date of Patent: May 5, 1987

[54] HYGIENIC SANITARY TOWEL

[76] Inventor: Georg Wiegner, Breslauer Strasse 35, 4060 Viersell 11, Fed. Rep. of Germany

[21] Appl. No.: 602,623

[22] Filed: Apr. 23, 1984

Related U.S. Application Data

[63] Continuation of Ser. No. 331,807, Dec. 17, 1981, abandoned, which is a continuation of Ser. No. 100,556, Dec. 5, 1979, Pat. No. 4,333,465.

[30] Foreign Application Priority Data

Dec. 9, 1978 [DE] Fed. Rep. of Germany ....... 2853243

[51] Int. Cl.$^4$ ............................................. A41B 13/02
[52] U.S. Cl. ..................... 604/380; 604/366; 604/370; 604/368; 604/382
[58] Field of Search ............... 604/370, 382, 381, 378, 604/379, 380

[56] References Cited

U.S. PATENT DOCUMENTS

| | | | |
|---|---|---|---|
| 1,979,899 | 11/1934 | O'Brien et al. | 128/284 |
| 2,067,961 | 1/1937 | Williams | 604/368 |
| 2,896,627 | 7/1959 | Harwood | 128/290 R |
| 3,230,955 | 1/1966 | Joa et al. | 128/290 R |
| 3,403,681 | 10/1968 | Hoey et al. | 128/290 R |
| 3,559,649 | 2/1971 | Grad et al. | 128/290 R |
| 3,888,254 | 6/1975 | Hendricks | 128/290 R |
| 3,994,299 | 11/1976 | Karami | 128/290 R |
| 4,055,180 | 10/1977 | Karami | 128/290 R |
| 4,176,667 | 12/1979 | Herring | 128/290 R |
| 4,232,674 | 11/1982 | Melican | 128/287 |
| 4,269,188 | 5/1981 | Nishizawa et al. | 128/287 |
| 4,285,342 | 8/1981 | Mesek | 128/287 |
| 4,333,464 | 6/1982 | Nakamo | 128/287 |

FOREIGN PATENT DOCUMENTS

132389 10/1979 Japan ................................. 128/287

Primary Examiner—C. Fred Rosenbaum
Assistant Examiner—Sherri Vinyard
Attorney, Agent, or Firm—Toren, McGeady and Goldberg

[57] ABSTRACT

A sanitary towel for absorbing body fluids composed of an absorptive hydrophilic fiber filling having a cover, the cover being composed of a liquid-impermeable composite material and having a defined liquid-permeable zone. The core of the filling material contains an insert having high absorptive polymers therein and being covered with a liquid-permeable woven carrier material, fleece or tissue. Such towels are easy to manufacture, highly absorptive and possess good tactile properties.

9 Claims, 15 Drawing Figures

HYGIENIC SANITARY TOWEL

This is a continuation of application Ser. No. 331,807, filed Dec. 17, 1981, now abandoned which, in turn, is a continuation of application Ser. No. 100,556, filed Dec. 5, 1979, now U.S. Pat. No. 4,333,465.

The invention relates to an hygienic sanitary towel for absorbing body fluids from a fluid outlet of the body with an absorptive filling of hydrophilic fiber materials and at least one cover, and the process for its manufacture.

Such hygienic sanitary towels are used in various constructions, for example, in baby hygiene as diapers or panties, in menstruation hygiene as sanitary napkins or as panty inserts and in medical practice as a dressing for absorbing the exudation of a wound or as a urinal sanitary towel. It is very important that these hygienic sanitary towels are comfortable to wear, agreeable to the skin, not too bulky and, as far as possible, do not develop odors. Since these sanitary towels are a disposable item, which is used relatively frequently, price and destructibility also play a role.

The user is frequently forced to wear such sanitary towels day and night for several days (sanitary napkins) or even over a long period of time (diapers, panty inserts, urinary sanitary towels). The use of hygienic sanitary towels therefore frequently leads to considerable discomfort, such as skin irritations, odor development or soiling of underwear and clothing. Moreover, users frequently feel inhibited or under a psychological stress as a result of the fact that people around them become aware of the use of the hygienic sanitary towels, for example, as a result of the fact that the sanitary towel is so bulky that it is visible through clothing or because the wearing of light clothing, especially of swimsuits, becomes impossible. On warm summer days, sweat frequently develops in the area of the sanitary towels and this can be very troublesome. Anxiety states may simply give rise to the notion that the sanitary towel no longer reliable absorbs the body fluid and that there may be seepage, which will be visible to everyone.

All in all, in spite of the considerable progress in the design of hygienic sanitary towels, which has been achieved in the past, a comprehensively satisfactory result has not yet been achieved. Such a result would presuppose that a product fulfils the following requirements optimally and simultaneously:
  (a) reliable prevention of seepage;
  (b) no significant, detectable odor formation;
  (c) pleasant wearing, no skin irritations;
  (d) small volume and therefore invisible, even when worn with light clothing;
  (e) economic to manufacture and therefore reasonably priced.

In the past, attempts to fulfil the preceding requirements for a sanitary towel in numerous cases have led, in respect to requirement (a), to products of voluminous design, which have adequate absorbency, but which fulfil neither requirement (d) nor requirement (e).

Plastic film has also already been used on the side of the sanitary towel away from the body, in order to prevent seepage. By these means however, the requirements for pleasant wearability and small volume (b and c) are not fulfilled and contact of the fluid with the skin is in no way precluded. This results from the fact that when plastic film is positioned around the outside of the cover, seepage cannot reliably be prevented in the case of, for example, sanitary napkins or diapers, because the position of the hygienic sanitary towel between the thighs adjusts to anatomical conditions and, accordingly, the edges of the sanitary towel come more or less into contact with underwear and clothing. This contact is reinforced by walking or kicking motions, so that, accordingly, the plastic film may slip to one side and fluid may be squeezed out. In addition, plastic films, positioned on the outside of the covering, frequently produce undesirable rustling effects.

In order to prevent contact of the fluid with the skin or clothing, hygienic sanitary towels have been produced with a hydrophobic cover. However, this measure brings little success, because hydrophobic covers do not provide a liquid-tight sanitary towel and because the fluids, which are stored initially, are squeezed out almost unimpededly by the movements of the body. The hydrophobic cover is merely able to achieve that fluid is not absorbed in wick-like fashion around the external circumference of the sanitary towel, as it is in the case of hydrophilic covers.

It is an object of the invention to provide a hygienic sanitary towel of the aforementioned type, which fulfils simultaneously and optimally the previously mentioned main requirements (a) to (e), which is easily handled in use as well as when positioning is or fixing it on the body, and which is easy and inexpensive to manufacture.

This objective is accomplished inventively by the fact that the outer cover consists of a liquid-impermeable composite material, has a defined liquid-permeable absorption zone on the side facing the fluid outlet and, in the core of the filling, contains an insert in which there are highly absorptive polymers.

That the new hygienic sanitary towel fulfils the set objectives in such an outstanding manner and meets all the requirements, is conditional on the combination of all the characteristics. The defined absorption zone in the region of the fluid opening of the body permits the fluid produced to enter exactly there, where it should be absorbed rapidly and completely. This concerted absorption is also supported by the insert of highly absorptive materials, which develops an absorbing and wicking effect throughout the absorptive zone and provides for a retention of the fluid within the interior of the hygienic sanitary towel. The fluid-impermeable cover, in the form of the composite material in the whole of the remaining region of the hygienic sanitary towel, on the other hand prevents the re-emergence of the fluid in the case of prolonged use and violent movements. From the point of view of the individual requirements, it turns out that:

The inventive hygienic towel first of all offers safety against seepage (requirement a). This is achieved owing to the fact that the sanitary towel, because of the fluid-impermeable finish of the cover and because of the highly absorbent insert, holds the body fluids in the specially created, relatively small, defined absorption zones as in a kind of moisture vault, without releasing them to the parts of the skin or clothing in contact with the sanitary towel.

The formation of odor (requirement b) is largely prevented in the new sanitary towel by the moisture-tight and odor-tight sealing of the absorbed fluids in the interior of the hygienic towel.

The new hygienic towel furthermore is pleasant to wear and represents no danger of irritating the skin (requirement c). By the extensive shielding of skin and underwear from contact with the fluid, skin irritations are prevented. The pleasant, soft nature of the carrier material of the outer cover is fully retained even in the composite material, because the impermeable layer is positioned at the inner side of the sanitary towel.

The sanitary towel moreover is small and can be worn even with light clothing (requirement d). Because the highly absorbent insert in the core of the sanitary towel is utilized to a high percentage, the sanitary towel can be made thinner and smaller than before, without running the risk of saturating it.

At the same time, the special construction and arrangement of the insert, according to the further development of the invention, plays a significant role. The insert preferably consists of tissue paper, which has been folded once or several times and on which, before the folding, highly abosrptive polymers are applied in granular or fiber form. These highly absorptive polymers are well known as such. They are capable of absorbing one hundred times their weight of liquid, without increasing their volume. For this purpose, two groups of materials particularly come into consideration, namely crosslinked carboxymethyl celluloses and polyacrylates. The latter are particularly preferred because they have outstanding absorptivity, even for blood. The highly absorptive polymers are preferably applied on an equally well absorbing material, for which cotton and tissue tape, which is especially preferred, come into consideration. This is a very good absorbent and therefore develops a wicking action and readily transmits the fluid, which is to be absorbed, to the highly absorptive polymers. The highly absorptive polymers are advisably enclosed in and retained by the tissue paper by repeatedly folding this paper.

It is particularly advantageous to provide the suitable tissue tape, which is preferred as a carrier material for the highly absorptive polymers, with a waffle pattern on a calender in order to create a large number of small pockets in which the highly absorptive polymer, particularly when it is used as a granulate, is accommodated. This embossing of the tissue tape can take place before the highly absorptive polymers are applied. However, the procedure is preferred in which the highly absorptive polymers are applied on a tissue tape of at least twice the width of the insert. The free edge region is then folded over, so enclosing the highly absorptive polymers. Only then is the waffle pattern embossed by calendering. The embossing creates the pockets in which the highly absorptive polymer preferably accumulates and, at the same time, bonds the two or three layers of tissue tape, obtained by the folding process, sufficiently firmly to each other. Because the highly absorptive polymers, lying loosely together as fibers or as a fine granulate, do not develop any mutual capillarity, the tissue paper with its wicking action action takes over the drainage of the fluid to the storage pockets with the highly absorptive polymers. These in turn absorb up to one hundred times their weight of fluid without increasing their volume appreciably and without releasing this fluid again, not even when subjected to squeezing.

Figure 6:
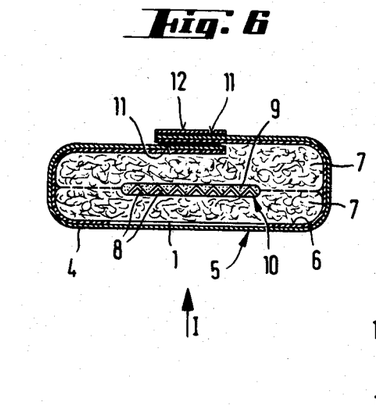
FIGS. 6 and 7 show cross sections through two different examples of the construction of the hygienic sanitary towel.
Figure 7:
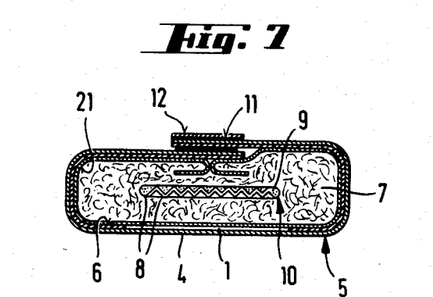
Figure 8:
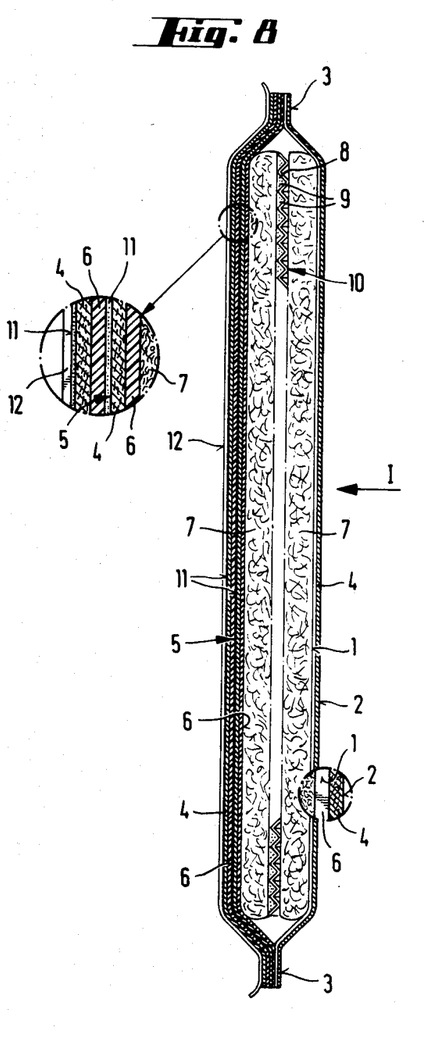
FIG. 8 shows a longitudinal section through the sanitary towel according to FIGS. 1 and 6.

This arrangement of this tissue tape, which contains the highly absorptive polymers in the core of the sanitary towel, as shown in FIGS. 6, 7 and 8, guarantees that the fluid will remain in the interior of the sanitary towel and, at the same time, avoids saturation and the development of any odors and, moreover, makes a particularly thin and small construction of the hygienic sanitary towel possible.

Finally, the hygienic sanitary towel is economic to manufacture and therefore inexpensive (requirement e). Because of the small size and the correspondingly small amount of material used, as well as because of the special construction of the internal cover, an economic manufacture on commercially available machines is possible. The new sanitary towel can therefore be offered very inexpensively.

The composite material, which forms the outer cover, preferably has the following construction. On the outside, it consists of a liquid-permeable carrier material of a woven fabric, fleece or tissue and therefore is decidedly skin compatible and comfortable to wear. With the exception of the defined absorption zone, it consists on the inside of a liquid-impermeable layer, which prevents passage of the fluid to the outside. At the same time, it is very important that the carrier material and the liquid impermeable layer are combined into a composite material, that is, that they do not lie loosely together as before, optionally bonded at the edge zones of the hygienic towel. Time and again, with the unavoidable movement of the body, this leads to emergence of the fluid between the layers and to a squeezing out of the fluid. Preferably, the carrier material is also made hydrophobic because, in the region of the defined absorption zone, it comes into direct contact with the fluid, which it should not absorb. In this connection, hydrophobic merely means that it absorbs no or only a little fluid. In spite of its hydrophobic finish, the carrier material allows the liquid, which is to be absorbed, to pass through under body contact and to be absorbed by the filling.

The inner, liquid-impermeable layer of the outer cover, that is, of the composite material, is preferably produced by laminating, calendering, extruding, coating, bonding or one-sided impregnating, printing or scattering. In this connection, bonding is understood to be the the application of a binding agent, for example, in the form of a plastic, or of a rubber latex. In the case of one-sided impregnation, the carrier material is allowed to contact the impregnating liquid only at the surface of the impregnating bath, so that the impregnation is not throrugh. Because of its simplicity and speed, the application of the liquid-impermeable layer by printing is especially preferred.

Materially, the liquid-impermeable layer preferably consists of plastic film, thermoplastic powders, thermoplastic pastes, hot or cold-setting adhesives, polyurethane, rubber, chemical bonding agents, impregnating agents or polyvinyl alcohol polymers of time-limited water stability, such as are produced from polyvinyl acetates by a quite specific degree of saponification. The time-limited water stability, which is achieved hereby, enables the hygienic sanitary towels, so finished, to be flushed away with much water, that is, they can be flushed away in a toilet.

Colored coatings, impregnations or bondings and printings have also proven their value, because they clearly delineate the impermeable regions from the permeable regions of the cover. The colored development of the liquid-impermeable layer has the advantage that embossings, such as, for example, trade marks, can also be applied.

In the case of the hygienic sanitary towel for absorbing body fluid, special importance is attached to the defined absorption zone and its refinement. Inventively, a type of window, the so-called absorption zone, is left blank in the outer cover of the liquid-impermeable, composite material, as a result of the fact that this region is left blank by the liquid-impermeable coating, and fluid can accordingly penetrate there. This liquid-permeable absorption zone can have a shape which matches the fluid outlet opening, which it is to cover. In certain circumstances however, the liquid, which is to be absorbed, can be prevented more reliably from seeping or running past by providing the absorption zone with absorption arms extending in all directions. In order to improve the drainage and to pass on the fluid to the highly absorptive insert, the adsorption zone itself may be perforated or needled.

The insert of the inventive hygienic sanitary towel consists in the interior of the filling, preferably of a tissue tape, which has been folded once or several times and on which the highly absorptive polymers are applied before folding in fiber form or in the preferred granulate form.

In so doing, a form of construction for the insert is especially preferred, in which a waffle patter is embossed in the singly or repeatedly folded tissue tape with a calender, so that the highly absorptive polymers in granulate form are stored in numerous small pockets and therefore are fixed very uniformly and immovably over the whole length and width of the insert. This introduction of the waffle patter can take place already before the addition of the highly absorptive polymers. Preferably however, the highly absorptive polymers are previously applied to the tissue tape, which is then folded once and preferably twice. Only then is the waffle pattern embossed by calendering. This has the advantage that the granulate collects in the pockets so formed and that, at the same time, the layers are bonded to each other.

It is however also possible and entirely advisable to anchor the highly absorptive polymers additionally on the tissue tape, for example, with an adhesive or by a careful wet treatment of the tissue tape. The amount of liquid, required for this purpose, is extremely small in comparison to the large amounts of liquid, which the highly absorptive polymers are capable of absorbing, so that their efficiency is not impaired to an appreciable extent by such a wet treatment.

That the highly adsorptive polymers preferably are applied on a tissue tape is justifed by the fact that tissue has an outstanding distribution action for liquids and develops a large wicking effect and so carries the fluid in an outstanding manner to the highly absorptive polymeric materials.

The particular advantage of this inventive refinement of the hygienic sanitary towel, especially of the exterior cover and the insert, consists moreover of the extreme economic efficiency of processing and manufacture. All previously known processes and machines for manufacturing hygienic sanitary towels process all components of the sanitary towel in one processing step on the machine. In particular, the various layers of the cover of the filling are supplied by rolls and must be arranged by accurately positioning them, turning them in, overlapping and gluing them, etc. around the hygienic sanitary towel. In so doing, the covering material, which has a relatively high surface smoothness, tends to slip aside. It is moreover obvious that the more individual components of a hygienic sanitary towel must be combined on one machine, the more complicated is the guidance of the machine and the more expensive the work load represented by threading, changing rolls and warehousing.

These deficiencies are largely avoided by the inventive covering material. Owing to the fact that the outer cover is designed as a composite material, the technical possibility exists of producing this composite material in a preliminary step, completely independently of the actual production machine for the hygienic sanitary towels.

This preliminary step of the operating procedure can be separated in terms of space and time from the later main step. Thus, in the case of a preferred process according to the most rational manufacturing techniques, material webs are manufactured in large machine widths, which are cut up later as required according to the various widths of the sanitary towels. The rolls, so cut up, can now be processed further on the hygienic sanitary towel machine at particularly high manufacturing speeds, because they 1. are, owing to the interlocking system, more stable than comparable materials supplied as multiple webs, In this connection, fleece+tissue+plastic film are to be regarded as is usual. Especially the plastic film, which is only 15–20$\mu$ thick, is inclined to be difficult to process owing to static charge, a smooth surface and instability. When laminated on the carrier material, that is, as a composite material, these difficulties are avoided.

2. permit a higher work intensity, once again owing to the use of a composite material as outer cover and due to the smaller number of work stations, the easier manipulations, the fewer roll changes, etc.

A highly preferred process for the manufacture of an inventive hygienic sanitary towel consists therefore in that on a carrier material, whose width is a multiple of the width of a cover, a large number of liquid-impermeable layers are applied so as to leave the absorption zones bare and combined into a composite material, then divided up into the number of individual webs corresponding to the multiple of the width of the cover and, in a separate processing step, the cover is folded around the filling containing the insert and finally cut up into the individual sanitary towels.

The particular advantage of this process lies in the fact that the wide webs of carrier material can be provided with a large number of liquid-impermeable layers, arranged side by side, in conventional, wide coating or printing equipment and combined into a composite material, without the speed of this process being dependent on the speed of the equipment for manufacturing the hygienic sanitary towel.

A preferred process for the manufacture of the insert with the highly absorptive polymers consists in that on a tissue tape of at least the twofold and preferably the threefold width of the insert, the highly absorptive polymers are applied across the width of the insert, the free edge zone or zones is or are folded over and that subsequently the waffle pattern is embossed by calendering and, afterwards, the individual layers of the tissue tape are combined with one another.

Further details of the invention are explained by means of the schematic representations of examples of the construction.

Figure 1:
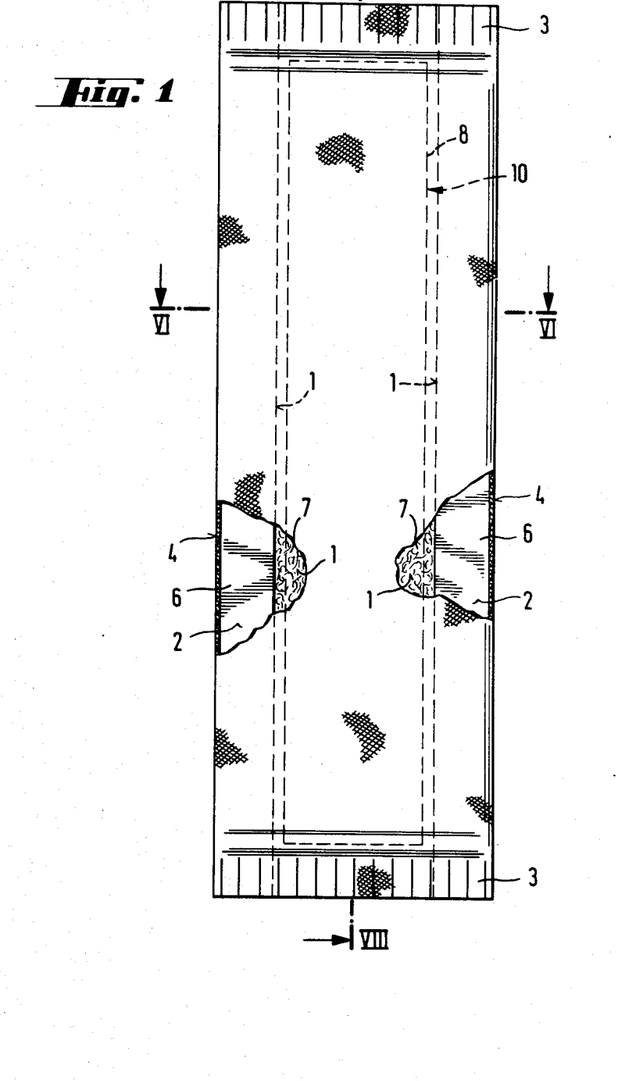
FIG. 1 shows the plan view of a hygienic sanitary towel with an absorption zone running straight through the center.

The drawing of FIG. 1 shows a hygienic sanitary towel in plan view with a straight absorption zone 1 running parallel to the longitudinal direction of the hygienic sanitary towel, liquid-impermeable regions 2 arranged on either side of the absorption zone 1 and closure zones 3 provided at the longitudinal ends.

Figure 2:
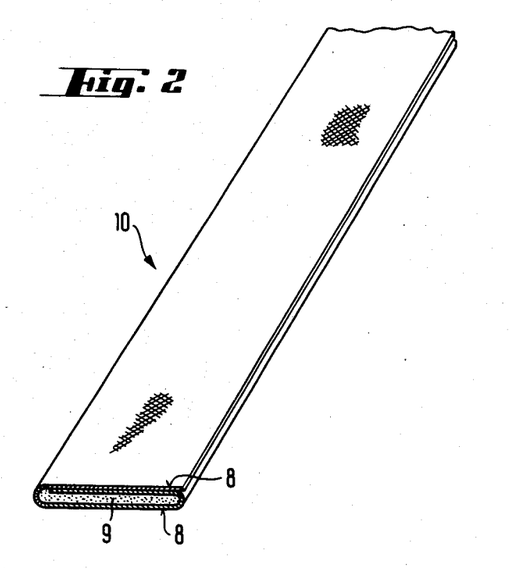
FIG. 2 shows a cross section and plan view of the insert in the form of a triply folded, highly absorptive tissue tape before the embossing.

FIG. 2 shows a cross section through the insert 10 of a highly absorptive tissue tape 8, in which the tissue tape 8 is folded twice so that the highly absorptive polymers 9 have a double cover of tissue on one side. The insert 10 has not yet been embossed and consolidated by calendering here.

Figure 3:
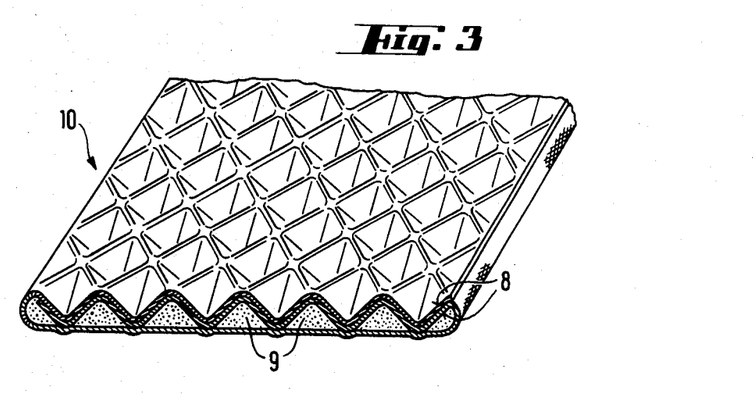
FIG. 3 shows an enlargement of a section of the insert of FIG. 2 after the waffle pattern has been embossed by calendering.

FIG. 3 shows the enlarged plan view of insert 10 with representation of the waffle pattern, the combination of the three layers of tissue brought about by the waffle calender and the associated formation of pockets.

Figure 4:
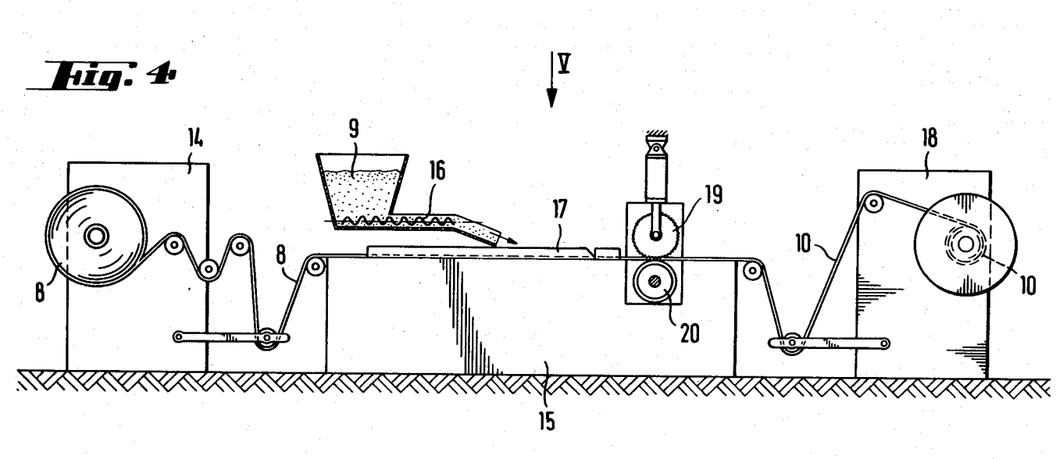
FIGS. 4 and 5 show the manufacture of the insert by the application of highly absorptive polymers on a tissue tape, in side elevation and plan view.
Figure 5:
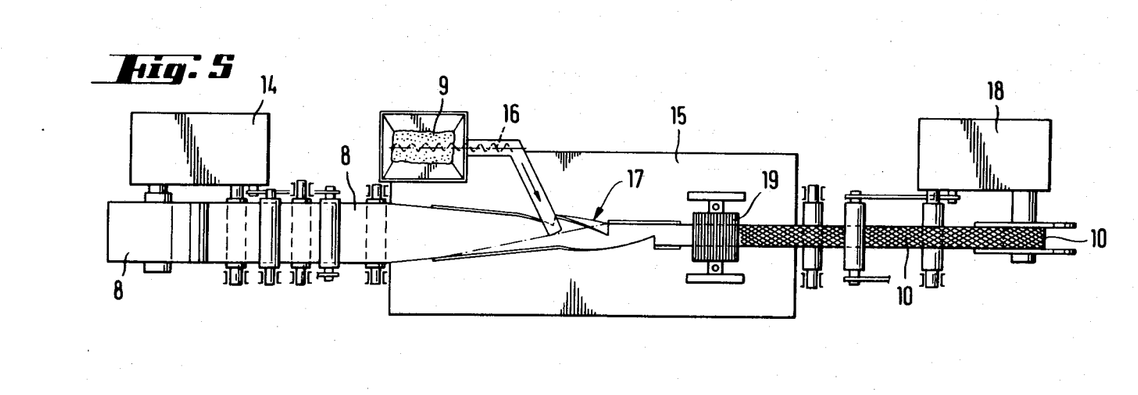

FIGS. 4 and 5 show the process for manufacturing the insert 10 and the application of the highly absorptive polymers 9.

The tissue tape 8 is supplied from an unwinding mechanism 14 to a scattering and folding unit 15 and the highly absorptive polymer is fed to the tissue tape 8 by means of a feeding screw 16. In the folding equipment 17, a third of the width of the web of the tissue tape 8 is then folded from the right and from the left over the middle third, so that the width of the insert 10 now results. This folded insert tape is now passed through the calender rollers 19, 20, of which the upper is the hard-steel roll 19, which embosses the waffle pattern, and the lower the soft calender roll 20. Insert 10, whose individual layers are bonded by calendering and embossing, is finally taken up on the take-up equipment 18 as an endless tape.

FIG. 6 shows a cross section through a hygienic sanitary towel according to FIG. 1. The absorption zone 1 here lies on the underside of the hygienic sanitary towel in the region in which the liquid-impermeable coating 6, which is provided on the inner side of the carrier material of the external cover 5, is discontinuous. The cover 5 is filled essentially with a filling 7 of hydrophilic fiber material, mainly cellulose fluff. In the core of filling 7, there is the insert 10, which consists of the tissue tape 8, which has been provided with the highly absorptive polymers 9. A glued seam, which is formed from an adhesive 11, for example, a hot melt, and a silicone paper 12, is provided on the side of the hygienic sanitary towel which lies opposite to the absorption zone 1.

The hygienic sanitary towel according to FIG. 7 is constructed quite similarly to that of FIG. 7. The essential difference consists of the fact that the filling 7 of cellulose fluff is enveloped once again in an enveloping tissue paper 21.

FIG. 8 shows the longitudinal section through a sanitary towel according to FIGS. 1 and 6, and moreover through the center of the hygienic sanitary towel, that is, through the region in which the defined absorption is left free from the coating 6. The tissue tape 8 is folded only once here around the layer with the highly absorptive polymers 9. At the same time, essentially the reference numbers of FIG. 4 have been used.

Figure 9:
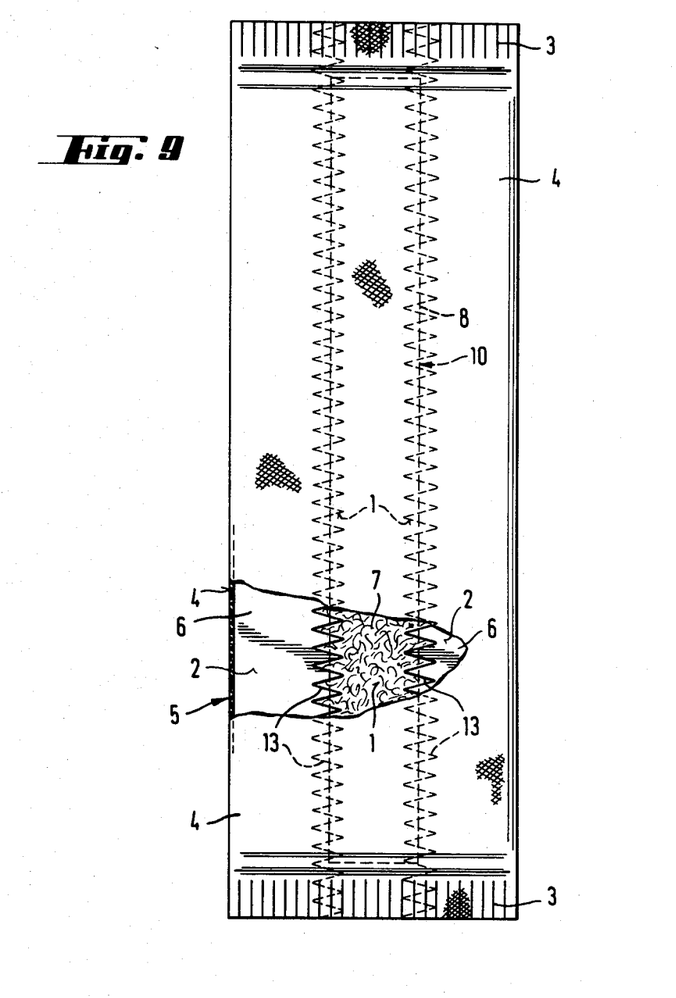
FIG. 9 shows a sanitary towel in plan view with a longitudinally arranged absorption zone with zigzag-shaped absorption arms.

The hygienic sanitary towel according to FIG. 9 differs from that of FIG. 1 especially due to the fact that the absorption zone 1 does not make straight boundaries with the liquid-impermeable regions 2, but zigzag-like boundaries 13, running in the longitudinal direction.

Figure 10:
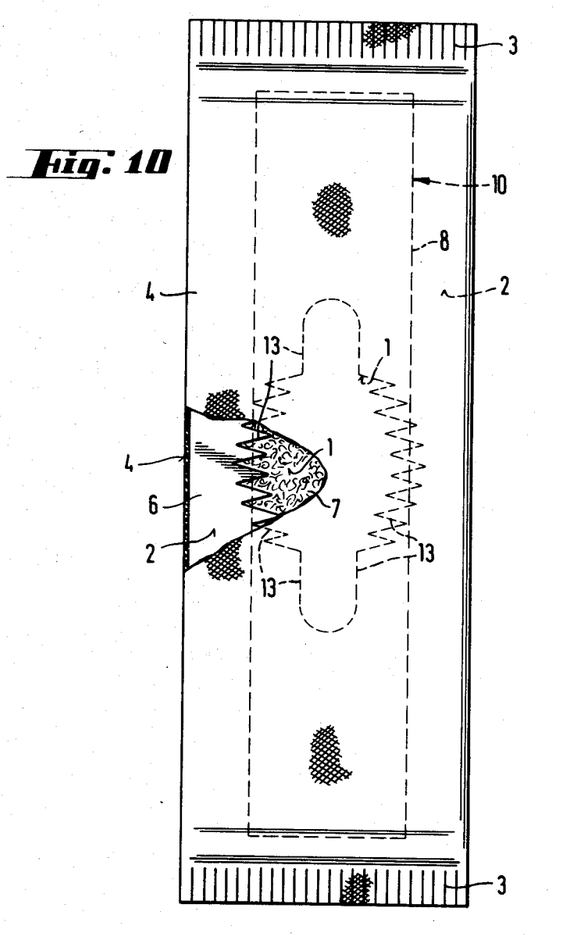
FIG. 10 shows a sanitary towel in plan view with an absorption zone with absorption arms arranged in star-shape fashion.

In the case of the hygienic sanitary towel of FIG. 10, the absorption zone 1 is located essentially centrally within a liquid-impermeable region 2. At the same time, the absorption zone 1 may have star-shaped absorption arms 13, which partially extend in the longitudinal direction of the hygienic sanitary towel and partially irregularly in the cross direction similarly to the longitudinal lines of FIG. 9. For this form of construction, the printing process for applying the liquid-impermeable coating 6 on the carrier material and so creating the impermeable regions 2, is particularly recommended.

Figure 11:
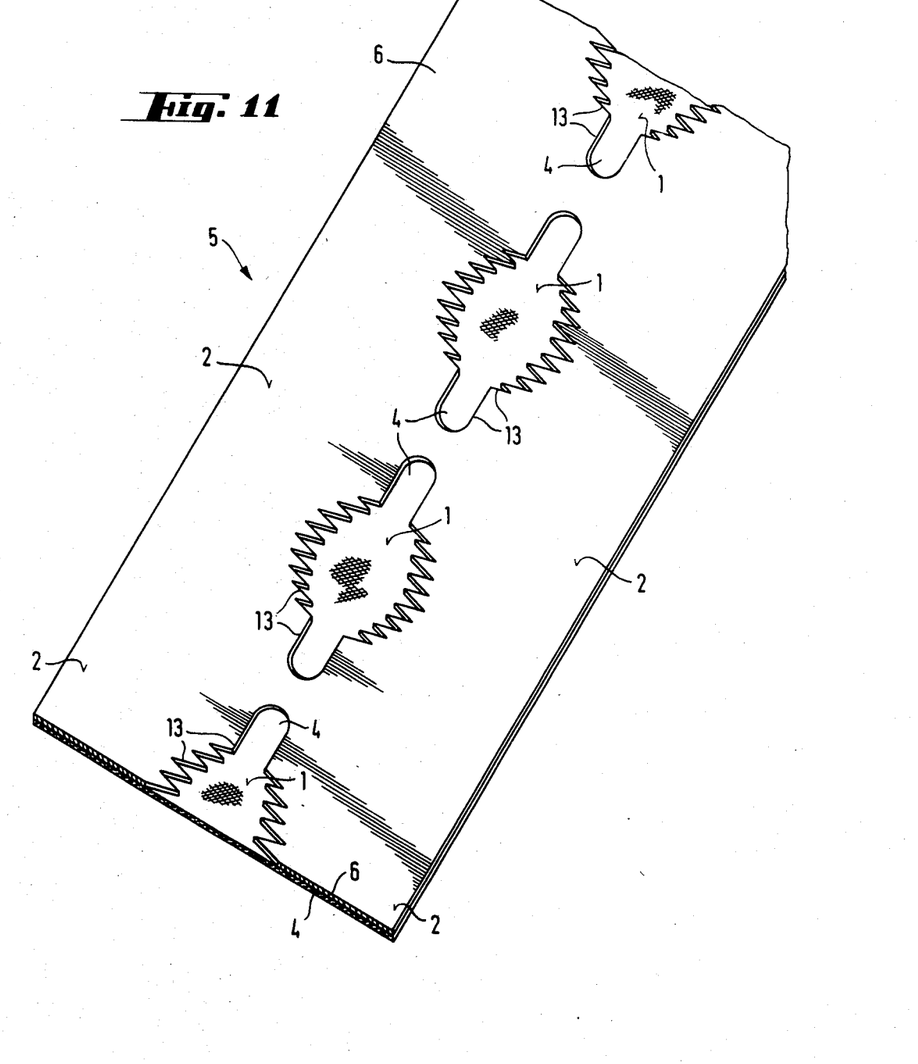
FIG. 11 shows a cross section and plan view of composite material of the outer cover.

FIG. 11 shows a cross section through the composite material of the outer cover 5 of carrier material 4 and coating 6, as well as the plan view of a section of the composite material in the running direction, in which the absorption zones 1 are visible.

Figure 12:
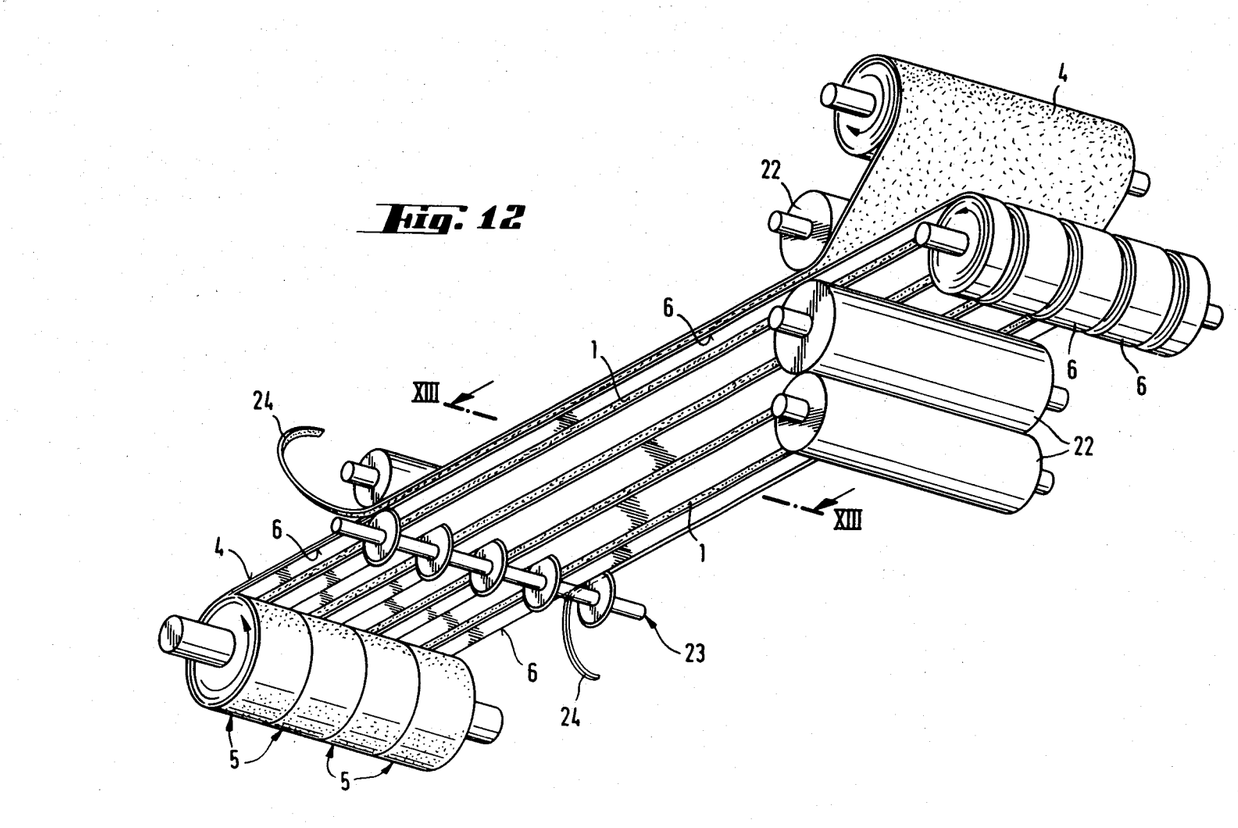
FIG. 12 shows the process for the manufacture of the composite material for the outer cover.

In FIG. 12, the process for the manufacture of the composite material for the outer cover 5, using a sanitary napkin as an example, is shown. On a hydrophobically finished carrier material 4 of four times the width of the outer cover 5 of an individual hygienic sanitary towel, 5 strips of a thin polyethylene film, 15μ thick, are laminated between rollers 22, the three inner strips being twice as wide at 105 mm than the two outer strips, which are 52.5 mm wide. The space between the strips of film, which forms the absorption zone 1, amounts to 35.5 mm. At both edges, an edge strip 24 of 20 mm remains unlaminated and is later removed with the edge cut. By cutting up the composite material in the longitudinal direction along the center of the wider of the applied strips of film by means of a longitudinal cutter 23, the wide web is then divided into four strips of composite material, each having the width of an outer cover 5, and wound up on a roll.

Figure 13:
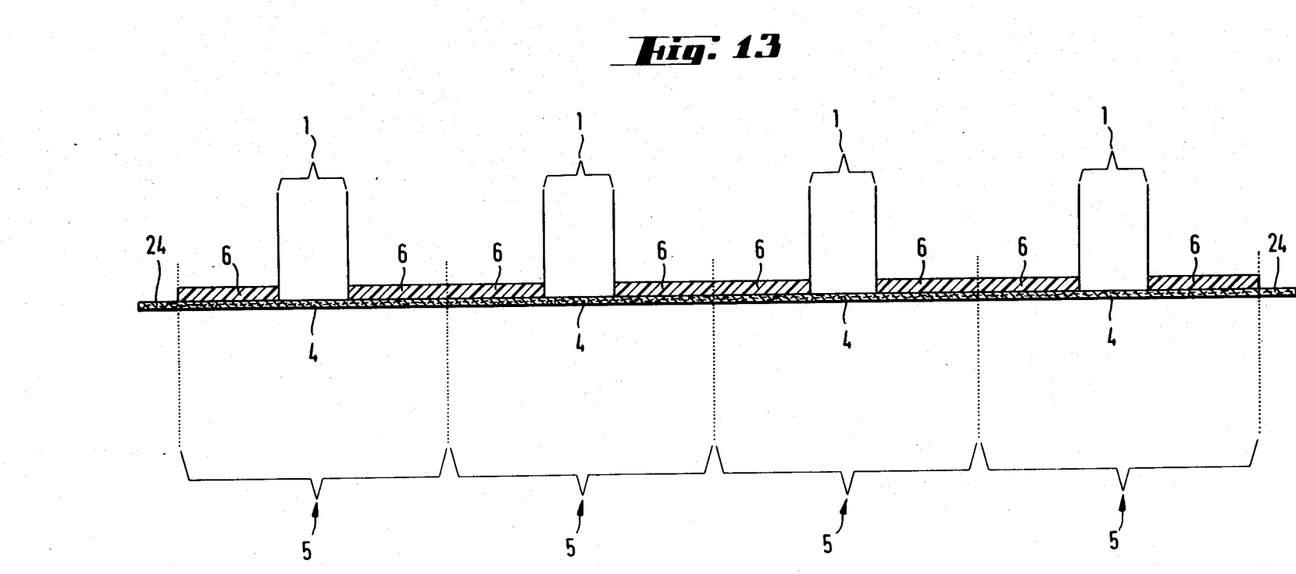
FIG. 13 shows a cross section through the composite material.

In FIG. 13, the longitudinal cutting up into individual webs of the outer cover 5 is indicated by dotted lines.

Figure 14:
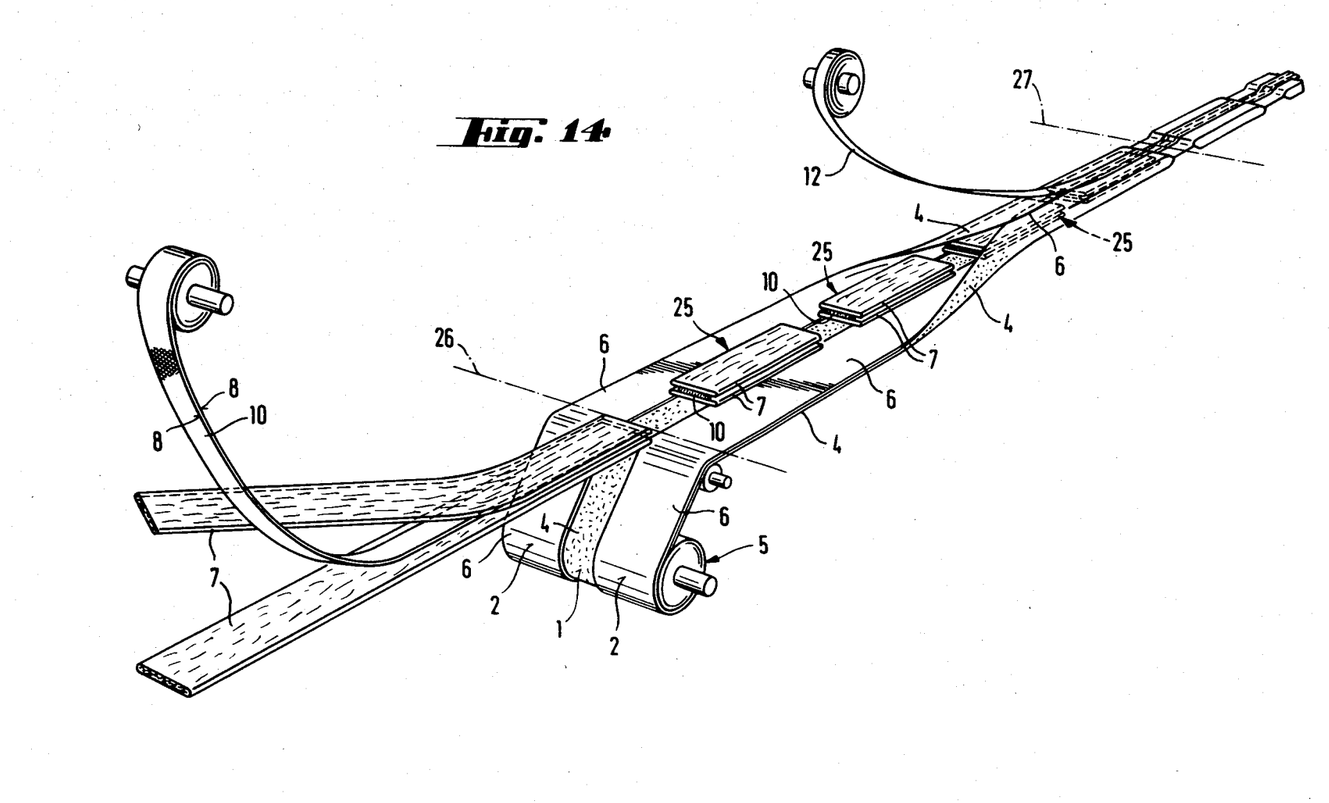
FIG. 14 shows the process for the manufacture of the hygienic sanitary towel.

FIG. 14 schematically shows the process of manufacturing the hygienic sanitary towel. Insert 10 is introduced between two strips of cellulose fluff which, combined together, from the filling 7. The composite material is supplied from below as the outer covering 5, and moreover in such a manner that the coating 6 faces upwards at the impermeable regions 2, that is, the carrier material lies at the bottom. The tape, consisting of filling 7 and insert 10, is cut at cutting site 26 with a cutting device, which is not shown, into individual cushions 25, which are placed consecutively, at a distance of about 2 cm, on the outer covering 5. The outer covering 5 is subsequently folded as a uniform composite material about the cushions 25 so that the edges, as can be seen in FIGS. 6 and 7, overlap somewhat. Ultimately, the silicone paper 12 is supplied and finally cut up at the cutting site 27 into the individual hygienic sanitary towels with simultaneous bonding by embossing of the ends of the outer covering 5, projecting front and rear.

I claim:

1. Hygienic sanitary towel for absorbing body fluid from a fluid opening of the body, consisting of an absorptive filling of hydrophilic fiber material with at least one cover, characterized by the fact that the outer cover (5) consists of a liquid-impermeable composite material and has a defined liquid-permeable absorptive zone (1) at the side facing the fluid opening, said filling having a core which contains an insert (10) in which there are highly absorptive polymers (9) and consists on the outside of a liquid-permeable carrier material (4) of woven material, fleece or tissue and, on the inside, with the exception of the defined absorption zone (1), of a liquid-impermeable layer (6) and wherein layer (6) of the outer covering (5), which is liquid-impermeable on the inner side, is produced by laminating, calendering, extruding, coating, bonding, impregnating on one side, printing or scattering, and material (4) and layer (6) are secured to the composite material and are not slidable with respect to one another, wherein outer cover (5) is wrapped about said core and the edges of cover (5) overlap and are secured to one another to form a seam, being on the side of the core opposite to said absorptive zone (1) and wherein said insert is manufactured by applying the highly absorptive polymers (9) on a tissue tape (8) of at least the twofold width of insert (10) across the width of insert (10), folding over any free edge regions, and thereafter, embossing a waffle pattern thereon by calendering to combine the individual layers of tissue tape (8) with one another.

2. Hygienic sanitary towel according to claim 1, characterized by the fact that the carrier material (4) of the outer cover (5) is finished hydrophobically.

3. Hygienic sanitary towel according to claim 1 or 2, characterized by the fact that the layer (6), which is liquid-impermeable on the inner side, is colored.

4. Hygienic sanitary towel according to claim 1 or 2, characterized by the fact that the layer, which is liquid-impermeable on the inner side, is formed from plastic film, thermoplastic powders, thermoplastic pastes, hot or cold-setting adhesives, polyurethane, rubber, chemical bonding agents, impregnating agents or polyvinyl alcohol polymers of time-limited water resistance.

5. Hygienic sanitary towel according to claim 1 or 2, characterized by the fact that the liquid-permeable absorption zone (1) has absorption arms (13), which are directed towards the side.

6. Hygienic sanitary towel according to claim 1 or 2, characterized by the fact that the liquid permeable absorption zone (1) is perforated or needled.

7. Hygienic sanitary towel according to claim 1 or 2, wherein the highly absorptive polymers (9) are anchored on a tissue tape (8) by an adhesive.

8. Hygienic sanitary towel according to claim 1 or 2, characterized by the fact that the highly absorptive polymers (9) are applied to a tissue tape (8) as a liquid.

9. Process for the manufacture of a hygienic sanitary towel according to claim 1, characterized by the fact that on a carrier material (4), whose width is a multiple of the width of a cover (5), at least two liquid-impermeable layers (6) are applied so as to leave the absorptive zones (1) bare and combined with the cover to form a composite material, then divided up into the number of individual webs corresponding to the multiple of the width of a cover (5) and, in a separate processing step, the cover (6) is folded around the filling (7) containing the insert (10) such that the edges of cover (5) overlap and are secured to one another to form a seam, said seam being formed on the side of the core opposite to absorptive zone (1), and finally cut up into the individual hygienic sanitary towels.

* * * * *